(12) United States Patent
Burke et al.

(10) Patent No.: US 9,844,773 B2
(45) Date of Patent: Dec. 19, 2017

(54) PICOLINAMIDE-CINCHONA ORGANOCATALYSTS AND DERIVATIVES

(71) Applicant: UNIVERSIDADE DE EVORA, Evora (PT)

(72) Inventors: Anthony Burke, Evora (PT); Pedro Miguel Cambeiro Barrulas, Evora (PT)

(73) Assignee: UNIVERSIDADE DE EVORA, Evora (PT)

( * ) Notice: Subject to any disclaimer, the term of this patent is extended or adjusted under 35 U.S.C. 154(b) by 0 days.

(21) Appl. No.: 15/026,170

(22) PCT Filed: Oct. 7, 2014

(86) PCT No.: PCT/IB2014/065128
§ 371 (c)(1),
(2) Date: Mar. 30, 2016

(87) PCT Pub. No.: WO2015/052656
PCT Pub. Date: Apr. 16, 2015

(65) Prior Publication Data
US 2016/0236184 A1    Aug. 18, 2016

(30) Foreign Application Priority Data

Oct. 8, 2013  (PT) .................................... 107209

(51) Int. Cl.
| | | |
|---|---|---|
| *C07D 453/02* | (2006.01) | |
| *C07D 453/04* | (2006.01) | |
| *B01J 31/02* | (2006.01) | |
| *B01J 35/00* | (2006.01) | |
| *C07C 209/00* | (2006.01) | |
| *C07C 213/00* | (2006.01) | |
| *C07F 7/18* | (2006.01) | |

(52) U.S. Cl.
CPC ....... *B01J 31/0247* (2013.01); *B01J 35/0033* (2013.01); *C07C 209/00* (2013.01); *C07C 213/00* (2013.01); *C07D 453/04* (2013.01); *C07F 7/1892* (2013.01); *B01J 2231/323* (2013.01); *B01J 2231/643* (2013.01); *B01J 2531/0269* (2013.01)

(58) Field of Classification Search
None
See application file for complete search history.

(56) References Cited

PUBLICATIONS

Carey, FA. Organic Chemistry 6th Ed. McGraw Hill. 2006, chapter 1, p. 9.*
Kocienski, PJ. et al. Protecting Groups. Thieme. 2005, p. 52.*
Nakamura, S. et al. Cinchona Alkaloid Amides/Dialkylzinc Catalyzed Enantioselective Desymmetrization of Aziridines with Phosphites. JACS. 2012, vol. 134, p. 19367.*
Nakamura, S. et al. Cinchona Alkaloid Amides/Dialkylzinc Catalyzed Enantioselective Desymmetrization of Aziridines with Phosphites-Supporting Information. JACS. 2012, vol. 134, p. 19367.*
S. Guizzetti, et al; Trichlorosilane-mediated stereoselective reduction of C=N bonds; European Journal of Organic chemistry; 2010; pp. 5529-5541.
M. Bonsignore, et al; Enantioselective reduction of ketoimines prompted by easily available (S)-proline derivatives; Beilstein Journal of Organic Chemistry; vol. 9; 2013; pp. 633-640.
O. Gleeson, et al; The immobilisation of chiral organocatalysts on magnetic nanoparticles: the support particle cannot always be considered inert; Organic & Biomolecular Chemistry; vol. 9; 2011; pp. 7929-7940.
M. Hayashi, et al; Cinchona alkaloid amides/dialkylzinc catalyzed enantioselective desymmetrization of aziridines with phosphites; Journal of the American Chemical Society; vol. 134; 2012; pp. 19366-19369.
International Search Report dated Jan. 26, 2015 for PCT/IB2014/065128.

* cited by examiner

*Primary Examiner* — Andrew D Kosar
*Assistant Examiner* — Ben S Michelson
(74) *Attorney, Agent, or Firm* — Lucas & Mercanti, LLP (57) ABSTRACT

The present application describes a novel type of picolinamide-cinchona organocatalyst that allows for the successful transformation of ketimines to chiral amines with very high enantioselectivities and with the highest TOFs reported for any particular organocatalyst to date. These organocatalysts have also been immobilized to a variety of solid supports, including magneto-nanoparticles.

4 Claims, 2 Drawing Sheets

PICOLINAMIDE-CINCHONA ORGANOCATALYSTS AND DERIVATIVES

CROSS REFERENCE TO RELATED APPLICATION

This Application is a 371 of PCT/IB2014/065128 filed on Oct. 7, 2014, which, in turn, claimed the priority of Portuguese Patent Application No. 107209 filed on Oct. 8, 2013, both applications are incorporated herein by reference.

TECHNICAL FIELD

The present application refers to an organocatalytic ketimine hydrosilylation process to chiral amines.

BACKGROUND

Organocatalysis is a subdivision of catalysis which relies on the use of wholly organic molecules as catalysts. These catalysts are very useful and have already made significant contributions in the production and discovery of new pharmaceuticals, agrochemicals and other high added value compounds (Alemán and Cabrera, 2013, MacMillan, 2008). The discovery of the Hajos-Parrish-Eder-Sauer-Wiechert reaction was the starting point (Eder et al. 1971, Hajos et al. 1974). But only relatively recently has there been a renaissance of this field, when Barbas III, Lerner, List and MacMillan applied very successfully simple small molecule organocatalysts (for example, L-proline and derivatives and imidazolidinones) in intermolecular aldol and Michael addition reactions, etc.

In general the catalysts are optically pure and the reactions highly enantioselective. Organocatalysts based on the Cinchona skeleton are known, and very good results have been reported for a diversity of reactions, like, conjugate additions (Hiemstra e Wynberg, 1981), Michael additions and Mannich reactions (Ye et al., 2005, Tillman et al. 2006, McCooey and Connon 2005), and phase-transfer catalysis (Chinchilla et al. 2000) amongst other reactions. Picolinamide based organocatalysts have also been reported and have been exploited with success in the hydrosilylation reaction of N-substituted imines (Guizzetti et al. 2009, Zheng et al. 2007) and in asymmetric Biginelli reactions (Xu et al. 2012).

Many chiral amines have been shown to be biologically active. 45% of molecules that chemists are developing into drugs contain a chiral amine unit (Ritter, 2013), well known examples include: rivastagimine, rasagline, sertraline, indatraline (Hyttel and Larsen, 1985) cetirizine and cromakilm etc.

Picolinamides, which are amides derived from picolinic acid have been incorporated into a number of carbon skeletons and used very successfully as organocatalysts in a number of reactions. For example in the asymmetric Biginelli reaction (Xu et al. 2012) in which the bifunctional organocatalyst of formula I:

(I)

which contains a primary amine linked to a picolinamide unit, is used in the reaction:

Another example is in the area of ketimine hydrosilylation using trichlorosilane as the reducing agent where the N-picolinoylaminoalcohol of formula II:

(II)

gave excellent results (Zheng et al. 2007) in the reaction with a catalyst loading of 10 mol %.

There are other examples in the literature (Guizzetti et al. 2009, Bonsignore et al. 2013, Onomura et al. 2006 and Jones and Warner, 2012). However, there aren't any reports on the synthesis and use of N-alkylated cinchona picolinamides.

The catalytic asymmetric hydrosilylation reaction of ketimines is extremely useful from an industrially perspective, as it affords chiral amines (Nugent and El-Shazly, 2010, Ghose et al. 1999), amino acids and other high valued products. Traditionally, the hydrogenation of ketimines is conducted using metal based catalysts (Nishiyama and Itoh, 2000). For decades, catalysis by way of metals has been the dominant form of catalysis, the principle advantages are that a variety of transition metals and ligands can be used and the catalysts tuned on this basis, and the loadings are generally low. Despite these advantages, the downside is that these catalysts are expensive, generally unstable to oxygen/water and to recycling, some are toxic and they generally end-up in the final product in small quantities (Busacca et al. 2011). This is less of a problem for most organocatalysts.

Quite recently, a number of groups have used organocatalysts in the hydrosilylation of ketimines, and have obtained good yields and enantioselectivities (Jones and Warner, 2012, Malkov et al. 2006, Bonsignore et al. 2013, Wang et al. 2006 and Wu et al. 2008). In fact, this methodology was nicely shown to be a viable approach to the commercial herbicide; (S)-Metolachlor (Guizzetti et al., 2009).

There have been several reports to date on the use of supported organocatalysts, (Cozzi, 2006, Kristensen and Tore, 2010), including the use of magnetic nanoparticles (Gleeson et al. 2011). However there have been no reports on the immobilization of picolinamide organocatalysts or derivatives.

The present disclosure describes a novel type of picolinamide-cinchona organocatalyst that allows for the successful transformation of ketimines to chiral amines with very high enantioselectivities and with the highest TOFs reported for any particular organocatalyst to date. These organocatalysts have also been immobilized to a variety of solid supports, including magneto-nanoparticles.

SUMMARY

The present application describes a novel type of picolinamide-cinchona organocatalyst that allows for the successful transformation of ketimines to chiral amines with very high enantioselectivities and with the highest TOFs reported considering any known organocatalyst to date. Thus, this application describes an organocatalyst comprising the formula:

(III)

in which,

⁓⁓⁓ represents a carbon-carbon single, double or triple bond;
R and $R^2$ represent, a hydrogen, an alkyl or alkyloxy chain, an aryl group, a nitro, a hydroxyl, an amine, a cyano or a halogen;
$R^1$ represents a hydrogen, an alkyl or an aryl group;
$R^3$ represents, an alkyl group;

the stereochemical configurations at C-8 and C-9, are the only ones that vary;
X represents, a halide, a triflate, a trifluoroborate, a $PF_6$, a $SbF_6$ or a $ClO_4$.

In an embodiment, the pyridyl ring of the above mentioned organocatalyst is fused with another benzene unit.

In another embodiment, the organocatalyst is immobilized with a suitable linker to a suitable support.

Still in a further embodiment, the linker is selected from the group comprising an alkyl, a polyoxyalkyl or a polyalkylsulfide chain and is linked to said organocatalyst at C-11 in (III).

In another preferred embodiment the support is selected from the group comprising silica gel, mesoporous silica, a soluble or insoluble polymer or a magnetic nanoparticle.

This application also describes the use of the described organocatalyst in catalytic asymmetric hydrosilylations of ketimines and derivatives.

Still in a further embodiment, the organocatalyst described above is used in the transformation of ketimines and derivatives into chiral amines with enantioseletivities up to 90% ee (enantiomeric excess).

BRIEF DESCRIPTION OF DRAWINGS

Without intent to limit the disclosure herein, this application presents attached drawings of illustrated embodiments for an easier understanding.

DESCRIPTION OF THE EMBODIMENTS

The present application describes the preparation of novel chiral organocatalysts of formula III:

(III)

in which,

R and $R^2$ represent, a hydrogen an alkyl or alkyloxy chain, an aryl group, a nitro, hydroxyl, amine, cyano or a halogen;
$R^1$ represents a hydrogen, an alkyl or an aryl group;
$R^3$ represents, an alkyl group.

The stereochemical configurations at C-8 and C-9, are the only ones that vary and the bond between C10 and C11 can be single, double or triple;

X represents, a halide, a triflate, a trifluoroborate, a $PF_6$, a $SbF_6$ or $ClO_4$.

The pyridyl ring can be fused with another benzene unit, according to the formula:

(III.a)

The chiral organocatalysts of formula III derive from the simple cinchona natural products, Cinchonidine (CD), Cinchonine (CN), Quinine (QN) and Quinidine (QD), where:

in which,

R and $R^2$ represent, a hydrogen an alkyl or alkyloxy chain, an aryl group, a nitro, hydroxyl, amine, cyano or a halogen;

$R^1$ represents a hydrogen, an alkyl or an aryl group;

$R^3$ represents, an alkyl group. The pyridyl ring can be fused with another benzene unit;

The stereochemical configurations at C-8 and C-9, are the only ones that vary and the bond between C11 and C12 can be single, double or triple;

X represents, a halide, a triflate, a trifluoroborate, a $PF_6$, a $SbF_6$ or $ClO_4$;

L represents a suitable linker, which can be an alkyl, polyoxyalkyl or a polyalkylsulfide chain, attached to a suitable support, like, silica gel, mesoporous silica, a soluble or insoluble polymer or a magnetic nanoparticle.

Cinchonidine(CD) R = H
Quinine (QN) R = OMe

Cinchonine (CN) R = H
Quinidine (QD) R = OMe

This invention also describes immobilized versions of (III), which are represented by formula IV.

The pyridyl ring can be fused with another benzene unit, according to the formula:

(IV)

(IV.a)

The organocatalysts of formula VIII and IX:

(VIII) in which X = I
(IX) in which X = BF$_4$

(VIII) in which X = I
(IX) in which X = BF$_4$ were synthesized, according to the reaction:

starting from cinchonidine (CD) and with 9-amino-(9-desoxi)-epi-cinchonidine (V) as an intermediate. The methylated picolonic acids (VI) and (VII) were prepared according to the previous reaction and were coupled with 9-amino-(9-desoxi)-epi-cinchonidine (V) a reaction that involved thermal condensation. However, other methods which involve coupling agents like carbonyldiimidazole (CDI), Mukaiyama's reagent, oxalyl chloride, thionyl chloride, P(OPh)$_3$ in which Ph is phenyl, dicyclohexylcarbodiimide (DCC)/NIC, 1-Ethyl-3-(3-dimethylaminopropyl)carbodiimide (EDC)/HOBt/diisopropylethylamine (DIPEA), N,N,N',N'-tetramethyl-O-(1H-benzotriazol-1-yl)uronium hexafluorophosphate (HBTU)/DIPEA, including many other coupling methods can be used. Various solvents, which ideally should be anhydrous can be used, like, CH$_2$Cl$_2$, THF, toluene etc.

In the case of the picolinic acid alkylations, numerous alkylating agents can be used, generally these are alkyl bromides, chlorides or iodides. However, Meerwein's reagent: triethyloxonium tetrafluoroborate, can also be used (to introduce an ethyl group). Alcoholic solvents give the best results.

(VIII)              (IX)

The iodide salt (VI) was readily converted to the trifluoroborate salt (VII) by a simple ion exchange process.

The corresponding non-N-alkylated derivative (X) was also prepared in 75% according to the reaction (Allen et al. 2012):

However, the coupling procedures given above can be used for this purpose.

With regard to the synthesis of the immobilized organocatalysts of formula (IV). Our approach was the use of ene-diene click chemistry (Hoyle and Bowman, 2010) to attach the organocatalyst to a trimethoxysilane based linker and then to the solid support. Three solid supports were investigated, nanosilica, MCM-41 and magnetic nanoparticles. The attachment of the linker involves the ene-diene reaction between the N-methylated picolinamide (IX) and (3-mercaptopropil)trimetoxisilane, using a catalytic quantity of 2,2'-azobisisobutyronitrile (AIBN) in chloroform (Tucker-Schwartz et al. 2011), these were found to be the optimized conditions.

The general strategy for immobilizing (IX) to the support is shown in the reaction:

TABLE 1

Screening results with catalysts (X), (VIII) and (I) for the hydrosilylation of N-phenyl 1-Phenylpropanimine (XII).

| Entry [a] | Catalyst | Yield(%) [b] | ee(%) [c] |
|---|---|---|---|
| 1 | (X) | 77 | 81 |
| 2 | (VIII) | 95 | 75 |
| 3 | (IX) | 83 | 84 |

[a] The reactions take-place at r.t. in the presence of 3 equivalents of $HSiCl_3$ in 1 mL de $CH_2Cl_2$ for 18 h.
[b] Isolated yields.
[c] Determined by HPLC using a chiral stationary phase.

Some very good yields are obtained (up to 95%) and an enantioselectivity of up to 84% ee (Table 1).

A variety of ketimines were used giving good results (Table 2).

TABLE 2

Screening results for the hydrosilylation of ketimines using the organocatalyst (IX) and a variety of ketimines

| Entry [a] | Ketimine | R | $R^1$ | $R^2$ | Yield (%) [b] | ee (%) [c] |
|---|---|---|---|---|---|---|
| 1 | (XII) | Ph | Et | Ph | 86 | 84 |
| 2 | (XIII) | Ph | Et | Tosyl | 73 | 73 |
| 3 | (XIV) | 4-MeO—$C_6H_4$ | Met | Tosyl | 30 | 55 |
| 4 | (XV) | Ph | Met | Tosyl | 11 | 50 |
| 5 | (XVI) | 2-HO—$C_6H_4$ | Met | Ph | 38 | 10 |
| 6 | (XVII) | 4-MeO—$C_6H_4$ | Met | Ph | 58 | 84 |
| 7 | (XVIII) | 4-MeO—$C_6H_4$ | Met | 4-Br$C_6H_4$ | 10 | 69 |
| 8 | (XIX) | 4-MeO—$C_6H_4$ | Met | 4-Br$C_6H_4$ | 20 | 69 |
| 9 | (XX) | 4-$NO_2$—$C_6H_4$ | Met | Ph | 68 | 80 |
| 10 | (XXI) | 4-$NO_2$—$C_6H_4$ | Met | 4-Br$C_6H_4$ | 9 | 58 |
| 11 | (XXII) | 4-$NO_2$—$C_6H_4$ | Met | 4-Br$C_6H_4$ | 75 | 76 |

[a] The reactions take-place at r.t. in the presence of 3 equivalents of $HSiCl_3$ in 1 mL de $CH_2Cl_2$ for 18 h.
[b] Isolated yields.
[c] Determined by HPLC using a chiral stationary phase.

In the case of the nanosilica, MCM-41 and silica-coated magnetic nanoparticle (SCMNP) supports, after the reaction was completed, the solids were filtered washed with $CH_2Cl_2$ (3×20 mL) and dried under vacuum at a temperature of 60° C. for 4 hours.

The organocatalyst loading was determined by microanalysis.

Figure 1:
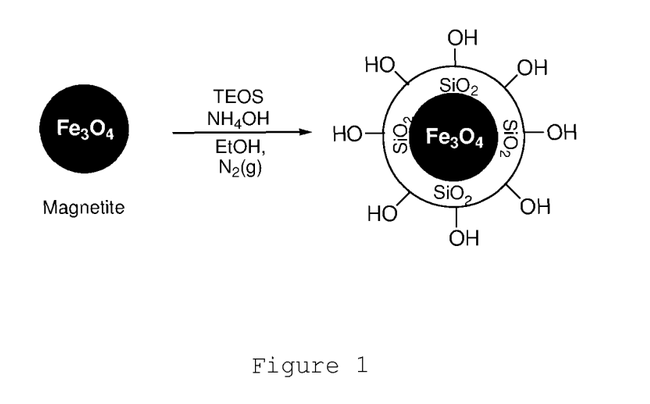
FIG. 1. Coating of magnetic iron oxide nanoparticles with a silica layer.
Figure 2:
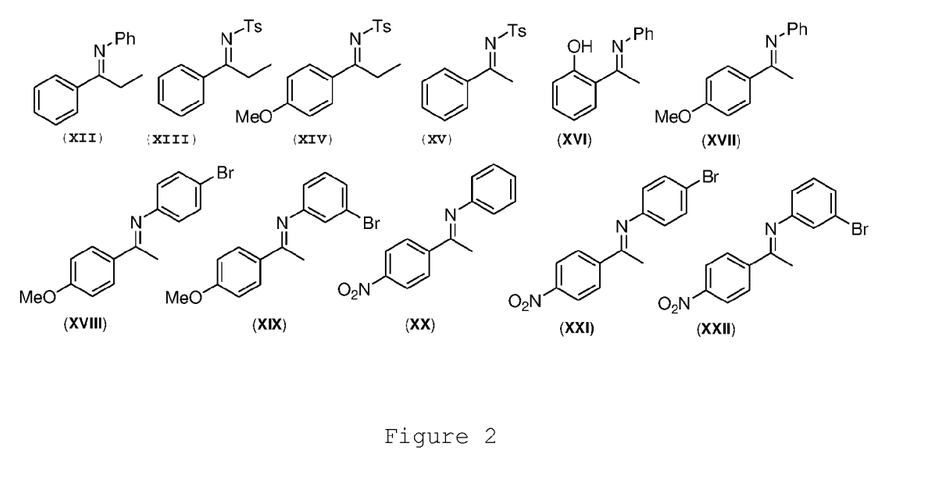
FIG. 2. Ketimines used in the hydrosilylation reaction with organocatalyst (IX).

With regard to the silica coated magnetic nanoparticles (SCMNPs), commercial magnetic iron oxide nanoparticles were used, and they were coated with a silica layer using literature methods (Lu et al. 2008, Schatz et al. 2009 and Zheng et al. 2009) (FIG. 1).

In the case of the catalytic reactions, our three catalysts were screened for the hydrosilylation of N-phenyl 1-Phenylpropanimine (XII) using trichlorosilane (Table 1)

The loading of the catalyst can be reduced to 0.5 mol % without any significant decrease in the yield and the enantioselectivity (Table 3). The turnover frequencies (TOF) and Asymmetric Catalyst Efficiency (ACE) (Eq. 1) (El-Fayyoumy et al., 2009) were determined.

$$ACE = \frac{MM_{product} \times ee \times \text{Yield}}{MM_{cat} \times \text{mol} \% \times 100} \qquad \text{(Equation 1)}$$

Significant was the enantioselectivity of 90% ee (Table 3, entry 7) using 1.5 equivalents of $HSiCl_3$.

TABLE 3

Screening results for the hydrosilylation of ketimine (XII) using various loadings of organocatalyst (IX)

| Entry [a] | Cat. (mol %) | $t_{rx}$ (h) | Yield (%) [b] | ee (%) [c] | TOF (mol · mol$^{-1}$ · h$^{-1}$) | TOF$_{max}$ (mol · mol$^{-1}$ · h$^{-1}$) | ACE | ACES (h$^{-1}$) |
|---|---|---|---|---|---|---|---|---|
| 1 | 20 | 18 | 85 | 85 | 0.24 | 0.28 | 1.53 | 0.08 |
| 2 | 10 | 18 | 86 | 84 | 0.48 | 0.56 | 3.05 | 0.17 |
| 3 | 5 | 18 | 88 | 82 | 0.98 | 1.11 | 6.09 | 0.34 |
| 4 | 1 | 18 | 86 | 80 | 4.78 | 5.56 | 29.06 | 1.61 |
| 5 | 0.5 | 18 | 78 | 72 | 8.67 | 11.1 | 47.43 | 2.64 |
| 6 | 0.1 | 18 | 53 | 18 | 29.4 | 55.6 | 40.29 | 2.24 |
| 7 [d] | 10 | 1 | 81 | 90 | 8.1 | 10 | 3.08 | 3.08 |
| 8 [d] | 5 | 1 | 67 | 88 | 13.4 | 20 | 4.98 | 4.98 |
| 9 [d] | 10 | 0.5 | 77 | 88 | 15.4 | 20 | 2.86 | 5.72 |
| 10 [d] | 10 | 0.25 | 54 | 87 | 30.8 | 40 | 1.98 | 7.94 |

[a] The reactions take-place at r.t. in the presence of 3 equivalents of HSiCl$_3$ in 1 mL de CH$_2$Cl$_2$ for 18 h.
[b] isolated yields.
[c] Determined by HPLC using a chiral stationary phase.
[d] The reactions take place with 1.5 equivs. of HSiCl$_3$.

The catalytic hydrosilylation of ketimine esters was also investigated giving very good yields and moderate to good enentioselectivities (Table 4).

TABLE 4

Screening results for the hydrosilylation of ketimine-esters (XXIII)-(XXVI) with HSiCl$_3$ and (IX).

| Entry [a] | Ketimine ester | n | R | R$^1$ | Yield (%) [b] | ee (%) [c] |
|---|---|---|---|---|---|---|
| 1 | (XXIII) | 1 | Meth | Meth | 73 | 23 |
| 2 | (XXIV) | 1 | Meth | Ethy | 82 | 23 |
| 3 | (XXV) | 1 | Ph | Ethy | 72 | 70 |
| 4 | (XXVI) | 0 | Ph | Ethy | 77 | 51 |

[a] The reactions take-place at r.t. in the presence of 3 equivalents of HSiCl$_3$ in 1 mL de CH$_2$Cl$_2$ for 18 h.
[b] isolated yields.
[c] Determined by HPLC using a chiral stationary phase.
[d] The reactions ocurr with 1.5 equivs. of HSiCl$_3$.

In the case of the immobilized catalysts the results are shown in Table 5.

TABLE 5

Screening results for the hydrosilylation of ketiminester (XII) with HSiCl₃ and immobilized organocatalyst (IX).

$$\text{(XII)} + HSiCl_3 \xrightarrow[CH_2Cl_2]{\text{Immobilized Cat. (10 mol \%)}} \text{product}$$

| Entry [a] | Immobilized (IX) | Cycle | Yield (%) [b] | ee (%) [c] | TOF (mol·mol⁻¹·h⁻¹) | TOF$_{máx}$ (mol·mol⁻¹·h⁻¹) | ACE | ACES (h⁻¹) |
|---|---|---|---|---|---|---|---|---|
| 1 | NSiO₂ | 1 | 47 | 34 | 0.26 | 0.57 | 0.37 | 0.02 |
| 2 | NSiO₂ | 2 | 50 | 38 | 0.28 | | 0.45 | 0.02 |
| 3 | NSiO₂ | 3 | 17 | 27 | 0.09 | | 0.11 | 0.01 |
| 4 | MCM | 1 | 71 | 37 | 0.39 | | 0.62 | 0.03 |
| 5 | MCM | 2 | 36 | 24 | 0.20 | | 0.20 | 0.01 |
| 6 | MCM | 3 | 47 | 8 | 0.26 | | 0.09 | 0.00 |
| 7 | MNP | 1 | 97 | 64 | 0.54 | | 1.46 | 0.08 |
| 8 | MNP | 2 | 30 | 50 | 0.28 | | 0.35 | 0.02 |
| 9 | MNP | 3 | 30 | 25 | 0.14 | | 0.18 | 0.01 |

[a] The reactions take-place at r.t. in the presence of 3 equivalents of HSiCl₃ in 1 mL de CH₂Cl₂ for 18 h.
[b] isolated yields.
[c] Determined by HPLC using a chiral stationary phase.
[d] The reactions ocurr with 1.5 equivs. of HSiCl₃.

One of the principle advantages of our catalytic system (particularly in the homogeneous phase) is the high enantioselectivities that can be obtained—up to 90% with excellent TOFs up to 40 mol·mol⁻¹·h⁻¹ (Table 3), the best so far reported for ketimine hydrosilylation.

In the case of the described immobilized catalyst systems their principal advantage is that the covalent attachment via the vinyl group on the cinchona unit, forces the reaction site to be significantly removed from the support, thus not limiting the reactivity of the organocatalysts.

EXPERIMENTAL EXAMPLES

Example 1: 2-(N-methyl)pyridinium iodide (VI)

On the basis of literature precedent (Shah et al. 2009), ácido picolínico (4.9 g, 39.80 mmol) was dissolved in iPrOH (30 mL) and this was followed by the addition of iodomethane (4.96 mL, 79.60 mmol). The reaction mixture was warmed to a temperature of between 50-55° C. and maintained at this temperature for 3 days. The temperature was then lowered and the title compound obtained as a yellow solid (5.26 g, 48%) after being filtered and washed with cold iPrOH and drying under vacuum.

$^1$H-NMR (400 MHz, DMSO-d₆): δ (ppm)=8.97 (d, 1H, J=4 Hz), 8.58 (t, 1H, J=8 Hz), 8.21 (d, 1H, J=8 Hz), 8.08 (t, 1H, J=8 Hz), 4.39 (s, 3H).

$^{13}$C-NMR (100 MHz, DMSO-d₆): δ (ppm)=161.4, 149.9, 146.7, 145.9, 127.4, 127.4, 47.1.

Example 2: 2-(N-methyl)pyridium tetrafluoroborate (VII)

According to the literature procedure (Shah et al. 2009) 2-(N-methyl)-pyridium iodide (1.056 g, 3.98 mmol) was dissolved in MeOH (20 mL) and stirred under an inert atmosphere. During the dissolution process AgBF₄ (1.738 g) in dry metanol (20 mL) was added. The flask was covered in aluminium foil during the ion exchange process. Once the solubilization process was complete, AgBF₄ was added dropwise until there was formation of a AgI precipitate. The initial brown coloured solution gave rise to a biphasic mixture with a light yellow coloured liquid phase and a yellow precipitate. The AgI salt was filtered and the filtrate was concentrated by evaporation in vacuo. The title compound was obtained as an oily off-yellow solid (0.824 g, 92%).

$^1$H-NMR (400 MHz, DMSO-d₆): δ (ppm)=8.68 (d, 1H, J=8 Hz), 8.46 (t, 1H, J=8 Hz), 8.05 (d, 1H, J=8 Hz), 7.91 (t, 1H, J=8 Hz), 4.27 (s, 3H).

$^{13}$C-NMR (100 MHz, DMSO-d₆): δ (ppm)=163.4, 147.0, 149.9, 128.2, 127.8, 47.9.

$^{19}$F-NMR (376 MHz, DMSO-d₆): δ (ppm)=−148.1.

Example 3: 9-O-mesylcinchonidine (III)

To a stirred solution of cinchonidine (10.032 g, 34.08 mmol) in anhydrous THF (350 mL) was added triethylamine (15 mL 107.6 mmol) and the solution was then cooled using an ice bath to aprox. 0° C. Methanesulphonyl chloride dissolved in a small quantity of THF was added dropwise to the mixture. Once this reagent was added, the reaction was stirred at room temperature for 2 h. The mixture was then quenched with 80 mL of a saturated solution of sodium bicarbonate and extracted with CH₂Cl₂. This was followed by column chromatography on silica gel using ethyl acetate as eluent to give the title compound as a with solid (11.760 g, 93%, mp 107.2-108° C.). $^1$H-NMR (400 MHz, CDCl₃): δ 8.94 (d, 1H, J=4 Hz, H2'), 8.28 (d, 1H, J=8 Hz, H5'), 8.15 (d, 1H, J=8 Hz, H8'), 7.75 (t, 1H, J=8 Hz, H7'), 7.66 (t, 1H, J=8 Hz, H6'), 7.52 (bs, 1H, H3'), 6.59 (bs, 1H, H9), 5.73 (m, 1H, J=12 Hz, H10), 5.00 (pseudot, 2H, H11), 3.45-3.32 (m, 2H, H6, H8), 3.11 (bs, 1H, H2), 2.76 (bs, 5H, H6, H2, $CH_3$ mesyl), 2.38 (bs, 1H, H3), 1.96-1.65 (m, 5H, H7, H5, H4). $^{13}$C-NMR (100 MHz, $CDCl_3$): δ 150.0 (C-2'), 148.8 (C-10'), 142.4 (C-10 endo), 140.1 (C-4'), 130.8 (C-8'), 129.9 (C-7'), 128.0 (C-9'), 125.1 (C-6', C-5'), 123.0 (C-3'), 115.6 (C-11 exo), 59.9 (C-9), 56.0 (C-8, C-2), 39.3 (C-6, C-3, mesyl), 27.2 (C-7, C-4, C-5), $[\alpha]_D^{21}$ −67.8 (c 1.03, $CH_2Cl_2$).

Example 4: (8S,9S)-9-azido-9-epicinchonidine (CDAZ)

9-O-Mesylcinchonidine (2.06 g, 5.53 mmol) was dissolved in anhydrous dimethylformamide (DMF) (40 mL) at room temperature, and this was followed by the addition of 2 equivalents of $NaN_3$ (0.719 g; 11.06 mmol) and the mixture was heated to 80° C. and stirred for 24 h. The solvent was then removed by distillation and the residue was re suspended in $H_2O$ (15 mL) and extracted with $CH_2Cl_2$ (3×10 mL), then purified by column chromatography on silica gel with ethyl acetate to furnish the title compound as a yellowish dense oil (1.701 g; 96%). $^1$H-NMR (400 MHz, $CDCl_3$): δ 8.95 (d, 1H, J=4 Hz, H2'), 8.23 (d, 1H, J=8 Hz, H5'), 8.18 (d, 1H, J=8 Hz, H8'), 7.77 (t, 1H, J=8 Hz, H7'), 7.65 (t, 1H, J=8 Hz, H6'), 7.41 (d, 1H, J=4 Hz, H3'), 5.76 (m, 1H, J=12 Hz, H10), 5.15 (d, 1H, J=10 Hz, H9), 4.99 (pseudot, 2H, J=13.2 Hz, H11), 3.35-3.21 (m, 3H, H6, H2, H8), 2.95-2.83 (m, 2H, H6, H2), 2.30 (bs, 1H, H3), 1.71-1.58 (m, 4H, H4, H7, H5), 0.77-0.72 (pseudoq, 1H, H7). $^{13}$C-NMR (100 MHz, $CDCl_3$): δ 150.0 (C-2''), 148.7 (C-10'), 142.2 (C-10 endo), 141.3 (C-4'), 130.6 (C-8'), 129.4 (C-7'), 127.2 (C-6'), 126.6 (C-9'), 123.0 (C-5'), 120.2 (C-3'), 114.4 (C-11 exo), 59.5 (C-9), 55.9 (C-8), 53.4 (C-2), 40.9 (C-6), 39.3 (C-3), 27.8 (C-7), 27.1 (C-4), 26.0 (C-5), $[\alpha]_D^{21}$ +42.1 (c 1.27, $CH_2Cl_2$).

Example 5: (8S,9S)-9-amino-9-epicinchonidine (VI)

9-azido-9-epicinchonidine (8.37 g, 26.2 mmol) was dissolved in 120 mL of anhydrous THF at room temperature, and this was followed by the slow addition of 1.5 equivalents of triphenylphosphine (10.18 g, 39.3 mmol) and was heated to 50° C. with stirring for 4 h. After complete consumption of the azide (CDAZ)), the mixture was allowed to cool to room temperature and then 3 mL of distilled water was added. The hydrolysis occurred overnight. After this, the excess of water was removed by the addition of anhydrous $MgSO_4$, followed by filtration and concentration of the organic phase. The product was purified by column chromatography on silica gel with AcOEt/MeOH/$NEt_3$ (100:2:3) to furnish the title compound as a yellowish dense oil (7.07 g, 92%). $^1$H-NMR (400 MHz, $CDCl_3$): δ (ppm)=8.92 (d, 1H, J=4 Hz, H2'), 8.36 (bs, 1H, H5'), 8.15 (d, 1H, J=8 Hz, H8'), 7.73 (t, 1H, J=8 Hz, H7'), 7.60 (t, 1H, J=8 Hz, H6'), 7.54 (bs, 1H, H3'), 5.82 (m, 1H, H10), 5.03-4.72 (m, 2H, H11), 4.72 (bs, 1H, H9), 3.33-3.22 (m, 2H, H6, H2), 3.10 (bs, 1H, H8), 2.85-2.82 (m, 2H, H6, H2), 2.42 (s, 2H, $NH_2$), 2.30 (bs, 1H, H3), 1.64-1.58 (m, 3H, H4, H7, H5), 1.43-1.41 (m, 1H, H5), 0.79-0.74 (m, 1H, H7). $^{13}$C-NMR (100 MHz, $CDCl_3$): δ (ppm)=150.5 (C2'), 148.8 (C10'), 141.8 (C10, C4'), 130.6 (C8'), 129.2 (C7'), 128.0 (C6'), 126.7 (C9'), 123.4 (C5'), 119.7 (C3'), 114.6 (C11), 62.1 (C9), 56.4 (C8), 41.1 (C6), 39.9 (C2), 29.8 (C3), 28.2 (C7), 27.7 (C4), 26.2 (C5).

Example 6: (8S,9S)-9-picolinamide(9-desoxy)-epi-cinchonidine (X)

(8S,9S)-9-Amino-9-epicinchonidine (1.064 g, 3.63 mmol) was dissolved in dry toluene (30 mL) to which was added commercial acid picolinic (0.446 g, 3.63 mmol) at room temperature giving a white suspension, the reaction was then subjected to a Dean-Stark distillation at a temperature of between 120-130° C. After 19 h the reaction became intensely orange in colour but transparent. The reaction was then cooled, and then concentrated on a rotary evaporator to give an orange spongy solid. This was then purified by silica gel column chromatography (AcOEt/MeOH (4:1)) affording the title compound as a white solid (1.08 g, 75%).
$^1$H-NMR (400 MHz, $CDCl_3$): δ (ppm)=9.04 (bs, 1H, HN), 8.88 (d, 1H, J=4 Hz, H2'), 8.57 (d, 1H, CH pyridine), 8.50 (d, 1H, CH pyridine), 8.12 (d, 1H, J=8 Hz, H5'), 8.02 (d, 1H, J=8 Hz, H8'), 7.75-7.68 (m, 2H, H7', CH pyridine), 7.62 (t, 1H, J=8 Hz, H6'), 7.51 (d, 1H, J=4 Hz, H3'), 5.78-5.64 (m, 2H, H10, H9), 5.00-4.93 (m, 2H, H11), 3.37-3.27 (m, 2H, H6, H2), 3.21 (bs, 1H, H8), 2.83-2.72 (m, 2H, H6, H2), 2.29 (bs, 1H, H3), 1.66-1.58 (m, 3H, H4, H7, H5), 1.42-1.29 (m, 1H, H5), 0.96-0.91 (m, 1H, H7).
$^{13}$C-NMR (100 MHz, $CDCl_3$): δ (ppm)=164.3 (C=O), 150.2 (pyridine), 149.8 (C2''), 148.7 (C10'), 148.3 (pyridine), 146.9 (C4'), 141.4 (pyridine), 137.3 (C10 endo), 130.5 (C8'), 129.2 (C7'), 127.5 (C6'), 126.9 (C9'), 126.2 (pyridina), 123.5 (pyridine), 122.3 (C5'), 119.6 (C3'), 1114.1 (C11 exo), 60.1 (C9), 56.0 (C8, C2), 41.1 (C6), 39.6 (C3), 27.9 (C7), 27.5 (C4), 26.2 (C5).

Example 7: (8S,9S)-9-[2-(N-methyl)pyridinium]-(9-desoxy)-epi-cinchonidine iodide (VIII)

This compound was prepared according to the method described in 6 using (8S,9S)-9-amino-9-epicinchonidine (1.128 g, 3.84 mmol) and 1.5 equivalents of 2-(N-methyl)pyridinium iodide (1.528 g, 5.76 mmol). The reaction mixture was purified by column chromatography on silica gel (AcOEt/MeOH (4:1)) giving the title compound as an oily orange solid (0.853 g, 43%).
$^1$H-NMR (400 MHz, $CDCl_3$+DMDO-d6): δ (ppm)=9.20 (bs, 1H, HN), 8.82 (d, 1H, J=4 Hz, H2'), 8.56 (d, 1H, CH pyridine), 8.48 (d, 1H, CH pyridine), 8.00 (d, 1H, J=8 Hz, H5'), 7.92 (d, 1H, J=8 Hz, H8'), 7.80 (t, 1H, J=8 Hz, H7'), 7.68 (t, 1H, J=8 Hz, H6'), 7.63-7.59 (m, 2H, H3', CH pyridine), 7.45-7.42 (m, 1H, CH pyridine), 5.79-5.71 (m, 2H, H10, H9), 5.02-4.92 (m, 2H, H11), 3.33 (m, 6H, H6, H2, H8, $^+$N—$CH_3$), 2.89-2.81 (m, 2H, H6, H2), 2.35 (bs, 1H, H3), 1.66 (bs, 3H, H4, H7, H5), 1.42 (bs, 1H, H5), 0.91 (bs, 1H, H7). $^{13}$C-NMR (100 MHz, $CDCl_3$+DMDO-d6): δ (ppm)=162.4 (C=O), 148.8, 148.2, 147.0, 146.9, 135.1, 135.2, 128.7, 128.6, 127.7, 125.7, 125.4, 125.1, 122.3, 122.2, 120.6, 113.5, 57.9, 53.7, 48.7, 39.7, 25.7, 24.2.

Example 8: (8S,9S)-9-[2-(N-methyl)pyridinium]-(9-desoxy)-epi-cinchonidine tetrafluorobate (IX)

This compound was prepared according to the method described in 6 using (8S,9S)-9-amino-9-epicinchonidine, (1.030 g, 3.51 mmol) and 1.5 equivalents of 2-(N-methyl)pyridinium tetrafluoroborate (1.184 g, 5.26 mmol). The reaction mixture was purified by column chromatography on silica gel (AcOEt/MeOH (4:1)) giving the title compound as an orange solid (0.828 g, 47%).
$^1$H-NMR (400 MHz, $CDCl_3$): δ (ppm)=9.03 (bs, 1H, HN), 8.85 (d, 1H, J=4 Hz, H2'), 8.46 (d, 1H, CH pyridine), 8.42 (d, 1H, CH pyridine), 8.12 (d, 1H, J=8 Hz, H5'), 8.01 (d, 1H, J=8 Hz, H8'), 7.76-7.71 (m, 2H, J=8 Hz, CH pyridine, H7'), 7.67-7.64 (m, 2H, J=8 Hz, CH pyridine, H6'), 7.32-7.29 (m, 1H, CH pyridine), 6.00 (bs, 1H, H9), 5.84-5.75 (m, 1H, H10), 5.13-5.07 (m, 2H, H11), 4.44 (bs, 3H, $^+$N—CH$_3$), 3.97 (m, 1H, H6), 3.67 (bs, 1H, H8), 3.51 (bs, 1H, H2), 3.19-3.15 (m, 1H, H6), 3.07-2.99 (m, 1H, H2), 2.51 (bs, 1H, H3), 1.83 (m, 3H, H4, H7, H5), 1.68 (m, 1H, H5), 1.08-1.03 (m, 1H, H7).

$^{13}$C-NMR (100 MHz, CDCl$_3$): δ (ppm)=164.9 (C=O), 150.6, 149.3, 148.8, 148.4, 144.6, 139.2, 137.4, 130.6, 129.6, 127.6, 127.1, 126.5, 123.3, 122.6, 119.9, 116.3, 59.8, 54.9, 41.7, 38.2, 29.8, 27.2, 26.2, 25.5.

$^{19}$F-NMR (376 MHz, CDCl$_3$): δ (ppm)=−145.5.

Example 9: (8S,9S)-9-[2-(N-methyl)pyridinium]-(9-desoxy)-(11-(3-(trimethoxysilylpropylthio)-epi-10,11-dihydrocinchonidine tetrafluoroborate (XI)

(8S,9S)-9-[2-(N-methyl)pyridinium]-(9-desoxy)-epi-cinchonidine tetrafluoroborate (IX) (0.4 g, 0.76 mmol) was dissolved in CHCl$_3$ (4 mL), to which was added (3-mercaptopropil)trimetoxisilane (0.142 mL, 0.76 mmol) and the stirred mixture was irradiated with uv light from a mercury vapor lamp for 24 h. The solvent and other volatile compounds were removed in vacuo, giving the title compound as a viscous orange oil (0.509 g, 96%) that was immobilized to the solid support.

MS (ESI): calculated for C$_{32}$H$_{45}$N$_4$O$_4$SSi$^+$ 611.30, observed value 611.27.

Example 10: Grafting of (8S,9S)-9-[2-(N-methyl)pyridium]-(9-desoxy)-epi-cinchonidine tetrafluoroborate (IX) to Nanosilica Gel Particles, MCM-41 and Magnetic Nanoparticles (8S,9S)-9-[2-(N-methyl)pyridinium]-(9-desoxy)-epi-cinchonidine tetrafluoroborate (IX) (0.180 g, 0.25 mmol) was placed in a 50 mL round bottom flask and dissolved in dry toluene. The support was then added [0.280 g (1.6% m/m)] and the mixture was refluxed under an inert atmosphere for 24 h.

(Nanosilica and MCM-41):

At the end of the reaction period the mixture was cooled and the solids were filtered and washed with CH$_2$Cl$_2$ (3×20 mL) followed by drying under reduced pressure with heating at 60° C. for 4 h.

Loadings (microanalysis) (Nanosilica)—0.340 mmol g$^{-1}$
(MCM-41)—0.405 mmol g$^{-1}$ Silica Coated MNPs:

The magnetic nanoparticles were prepared according by a literature method (Zeng et al. 2011). At the end of the reaction period the mixture was cooled and the solids were filtered and washed with CH$_2$Cl$_2$ (3×20 mL) followed by drying under reduced pressure with heating at 60° C. for 4 h.

Loading (microanalysis)—0.470 mmol g$^{-1}$

Example 11: Catalytic Homogeneous Asymmetric Hydrosilylation of N-phenyl 1-Phenylpropanimine (XII)

N-phenyl 1-Phenylpropanimine (XII) (100 mg, 0.42 mmol) was dissolved in CH$_2$Cl$_2$ (2 mL) to which was added the organocatalyst (IX) (10 mol %). The reaction mixture was then cooled on an ice-bath and after 15 minutes the HSiCl$_3$ (3 equivs) was added drop-wise. Once the addition was complete the reaction mixture was stirred at room temperature for 21 h. The reaction was quenched by the addition of a saturated solution NaHCO$_3$ (2 mL). The organic phase was extracted with CH$_2$Cl$_2$ (3×10 mL) dried with anhydrous MgSO$_4$, filtered and evaporated to dryness in vacuo. The resulting residue was purified by column chromatography with silica gel (CH$_2$Cl$_2$) affording (R)—N-phenyl-1-phenylpropyl-1-amine (86 mg, 86%) as a colourless oil.

$^1$H-NMR (400 MHz, CDCl$_3$) δ 7.39 (m, 4H), 7.28 (m, 1H), 7.14 (t, 2H), 6.69 (t, 1H), 6.59 (d, 2H), 4.29 (t, 1H), 4.13 (bs, 1H), 1.89 (m, 2H), 1.02 (t, 3H).

$^{13}$C NMR (101 MHz, CDCl$_3$) 147.63, 144.04, 129.20, 128.61, 127.00, 126.60, 117.24, 113.36, 59.84, 31.78, 10.95.

HPLC (Daicel Chirapak OD-H, hexane/isopropanol=80:20, fluxo 1 mL/min), λ=254 nm: t$_R$=4.91 min (minor enantiomer), t$_S$=5.46 min (major enantiomer).

Example 12: Catalytic Heterogenous Asymmetric Hydrosilylation of N-phenyl 1-Phenylpropanimine (XII)

According to the procedure described in Example 11, the immobilized catalysts were added at a loading of 10 mol % to the 1-Phenylpropanimine (XII) substrate in CH$_2$Cl$_2$, and this was followed by the dropwise addition of HSiCl$_3$. At the end of 18 h at room temperature, the reaction was worked up by filtering off the supported catalyst (which was dried under vacuum at 60° C. for 1 h, so that it is available to be reused in subsequent cycles) and subjecting the crude product to a work-up as described in Example 11. The resulting residue was purified by column chromatography with silica gel (CH$_2$Cl$_2$) affording (R)—N-phenyl-1-phenylpropyl-1-amine (97 mg, 97%) as a colourless oil.

BIBLIOGRAPHY

J. Alemán, S. Cabrara, Chem. Soc. Rev. 2013, 42, 774-93.
C. L. Allen, A. R. Chhatwal, J. M. J. Williams, Chemical Communications 2012, 48, 666-668.
M. Bonsignore, M. Benaglia, L. Raimondi, M. Orlandi, G. Celetano, Beilstein—J. Org. Chem. 2013, 9, 633-40.
C. A. Busacca, D. R. Fandrick, J. J. Song, C. H. Senanayake, Adv. Synth. Catal. 2011, 353, 1825-64.
R. Chinchilla, P. Mazón, C. Nájera, Tetrahedron: Asymm. 2000, 3277-81.
F. Cozzi, Adv. Synth. Catal. 2016, 348, 1367-90.
U. Eder, G. Saurer, R. Wiechert, Angew. Chem. Int. Ed. Engl. 1971, 10, 496-7.
S. El-Fayyoumy, M. H. Todd, C. J.; Richards, Beilstein Journal of Organic Chemistry 2009, 5, 67-.
A. K. Ghose, V. N. Viswanadhan, J. J. Wendoloski, J. Comb. Chem. 1999, 1, 55-68.
O. Gleeson, G-L. Davies, A. Peschiulli, R. Tekoriute, Y. K. Gun'ko, S. J. Connon, Org. Biomol. Chem. 2011, 9, 7929-40.
S. Guizzetti, M. Benaglia, F. Cozzi, R. Annunziata, Tetrahedron, 2009, 65, 6354-63.
I. E. Kristensen, T. Hansen, Eur. J. Org. Chem., 2010, 3179-204.
S. Jones, C. J. A. Warner, Org. Biomol. Chem. 2012, 10, 2189-2200.
S. H. McCooey, S. J. Connon, Chem. Commun, 2005, 4481-3.
D. W. C. MacMillan, Nature, 2008, 455, 304-8.
Z. G. Hajos, D. R. Parrish, J. Org. Chem. 1974, 39, 1615-21.

H. Hiemstra, H. Wynberg, *J. Am. Chem. Soc.* 1981, 103, 417-30.

C. E. Hoyle, C. N. Bowman *Angew. Chem. Int. Ed. Engl.* 2010, 49, 1540-1573.

J. Hyttel, J. J. Larsen, *J. Neurochem.* 1985, 44, 1615-22.

S. Luo, X. Zheng, J. Cheng, *Chem. Commun,* 2008, 5719-5721.

A. V. Malkov, S. Stončus, K. N. MacDougall, A. Mariani, G. D. McGeoch, P. Kočovský, *Tetrahedron,* 2006, 62, 264-84.

H. Nishiyama, K. Itoh, *Asymmetric Hydrosilylation and related reactions em Catalytic Asymmetric Synthesis,* I. Ojima (Ed.), 2nd edition, Cap. 2, pp 11-43, Wiley-VCH, Inc., New York, 2000.

T. C. Nugent, M. El-Shazly, *Adv. Synth. Catal.* 2010, 352, 753-819.

S. K. Ritter, *Chem. Eng News,* Jul. 29, 2013 pp 34.

Shah, J.; Khan, S. S.; Blumenthal, H.; Liebscher, J. *Synthesis-Stuttgart* 2009, 3975-3982.

Schätz, A.; Hager, M.; Reiser, O. *Advanced Functional Materials* 2009, 19, 2109-2115.

A. L. Tillman, J. Ye, D. J. Dixon, *Chem. Commun.* T2006, 1191-3.

A. K. Tucker-Schwartz, R. A. Farrell, R. L.; Garrell, *J. Am. Chem. Soc.* 2011, 133, 11026-11029.

J. Ye, D. J. Dixon, P. S. Hynes, *ChemComm.* 2005, 4481-3.

Zeng, T.; Yang, L.; Hudson, R.; Song, G.; Moores, A. R.; Li, C. *Organic Letters* 2011, 13, 442-445.

Naturally, the present application is by no means restricted to the embodiments described in this document, and a person with average skills in the art might predict many possibilities of altering the same without departing from the general idea, as defined in the claims.

All the embodiments described above may obviously be combined with each other. The following claims additionally define preferred embodiments.

The invention claimed is:

1. An organocatalyst of the formula:

(III)

wherein,

～～～ represents a carbon-carbon single, double or triple bond;

R represents a hydrogen, a hydroxyl or an alkyl chain;

$R^2$ represents a hydrogen, an alkyl, a nitro, hydroxyl, amine, cyano or a halogen;

$R^1$ represents a hydrogen;

$R^3$ represents an alkyl group;

the stereochemical configurations at C-8 and C-9, are the only ones that vary;

X represents, a halide, a triflate, a trifluoroborate, a $PF_6$, a $SbF_6$ or a $ClO_4$.

2. An organocatalyst wherein a pyridyl ring is fused with a benzene unit thereby providing the following formula IIIa wherein, ～～～ represents a carbon-carbon single, double or triple bond;

R represents a hydrogen, a hydroxyl or an alkyl chain;

$R^1$ represents a hydrogen;

$R^2$ represents a hydrogen, an alkyl, a nitro, hydroxyl, amine, cyano or a halogen;

$R^3$ represents an alkyl group;

the stereochemical configurations at C-8 and C-9, are the only ones that vary; and X represents, a halide, a triflate, a trifluoroborate, a $PF_6$, a $SbF_6$ or a $ClO_4$.

3. An organocatalyst of the formula IV (IV)

wherein

～～～ represents a carbon-carbon single, double or triple bond;

R represents a hydrogen, a hydroxyl or an alkyl chain;

$R^2$ represents a hydrogen, a nitro, hydroxyl, amine, cyano or a halogen;

$R^1$ represents a hydrogen;

$R^3$ represents an alkyl group;

the stereochemical configurations at C-8 and C-9, are the only ones that vary;

X represents, a halide, a triflate, a trifluoroborate, a $PF_6$, a $SbF_6$ or a $ClO_4$;

L represents a linker; and
said organocatalyst is immobilized with the linker to a support and the linker is attached to said organocatalyst at C-11,
wherein the linker is an alkyl, a polyoxyalkyl or a polyalkylsulfide chain.

4. The organocatalyst according to claim 3, wherein the support is silica gel, mesoporous silica, a soluble or insoluble polymer or a magnetic nanoparticle.

* * * * *